(12) United States Patent
Phipps et al.

(10) Patent No.: US 9,943,820 B2
(45) Date of Patent: Apr. 17, 2018

(54) MICROCAPSULES

(71) Applicant: IMERYS MINERALS LIMITED, Par Cornwall (GB)

(72) Inventors: Jonathan Stuart Phipps, Cornwall (GB); Robert Urquhart, Isle of Skye (GB)

(73) Assignee: Imerys Minerals Limited, Par Cornwall (GB)

( * ) Notice: Subject to any disclaimer, the term of this patent is extended or adjusted under 35 U.S.C. 154(b) by 0 days.

(21) Appl. No.: 14/406,473

(22) PCT Filed: Jun. 7, 2013

(86) PCT No.: PCT/GB2013/051504
§ 371 (c)(1),
(2) Date: Dec. 8, 2014

(87) PCT Pub. No.: WO2013/182855
PCT Pub. Date: Dec. 12, 2013

(65) Prior Publication Data
US 2015/0190774 A1 Jul. 9, 2015

(30) Foreign Application Priority Data

Jun. 8, 2012 (GB) .................................. 1210156.4
Jun. 22, 2012 (GB) .................................. 1211142.3

(51) Int. Cl.
| | | |
|---|---|---|
| *B01J 13/22* | (2006.01) | |
| *C11B 9/00* | (2006.01) | |
| *A01N 25/28* | (2006.01) | |
| *A61K 8/11* | (2006.01) | |
| *B01J 13/14* | (2006.01) | |
| *C11D 17/00* | (2006.01) | |
| *A61Q 19/00* | (2006.01) | |
| *A61K 8/87* | (2006.01) | |
| *A23P 10/30* | (2016.01) | |
| *A23L 27/00* | (2016.01) | |
| *A61Q 5/02* | (2006.01) | |
| *A61Q 17/04* | (2006.01) | |

(52) U.S. Cl.
CPC .............. *B01J 13/22* (2013.01); *A01N 25/28* (2013.01); *A23L 27/72* (2016.08); *A23P 10/30* (2016.08); *A61K 8/11* (2013.01); *A61K 8/87* (2013.01); *A61Q 19/00* (2013.01); *B01J 13/14* (2013.01); *C11B 9/0019* (2013.01); *C11D 17/0039* (2013.01); *A61K 2800/10* (2013.01); *A61K 2800/412* (2013.01); *A61Q 5/02* (2013.01); *A61Q 17/04* (2013.01)

(58) Field of Classification Search
CPC ......... A01N 25/28; A01N 53/00; B01J 13/04; B01J 13/14; B01J 13/22; A61Q 17/00; A61Q 17/04; A61Q 5/02; A61Q 19/00; Y10S 977/773; A23L 27/72; A23P 10/30; A61K 8/11; A61K 8/87; A61K 2800/10; A61K 2800/412; C11D 17/0039; C11B 9/0019
USPC ........ 428/402–402.24, 403, 404, 407, 321.1, 428/474.4; 427/331, 389.9, 212, 427/213–213.36, 483, 256; 264/534, 5, 264/41, 4–4.7; 424/400, 408, 450, 451, 424/455, 93.7, 184.1, 497, 489, 501, 490, 424/491, 493, 494, 495, 492
See application file for complete search history.

(56) References Cited

U.S. PATENT DOCUMENTS

| | | |
|---|---|---|
| 3,577,515 A | 5/1971 | Vandegaer |
| 4,076,774 A | 2/1978 | Short |
| 4,285,720 A | 8/1981 | Scher |
| 2003/0193102 A1 | 10/2003 | Yan |
| 2005/0067726 A1* | 3/2005 | Yan ........................ A23L 1/0029 264/4.1 |
| 2011/0200658 A1* | 8/2011 | Mulqueen .............. A01N 25/28 424/408 |

FOREIGN PATENT DOCUMENTS

| | | |
|---|---|---|
| CN | 1986721 A | 6/2007 |
| CN | 102617769 A | 8/2012 |

(Continued)

OTHER PUBLICATIONS

International Search Report and Written Opinion dated Apr. 24, 2014, for International Application No. PCT/GB2013/051504.

(Continued)

*Primary Examiner* — Irina S Zemel
(74) *Attorney, Agent, or Firm* — Finnegan, Henderson, Farabow, Garrett & Dunner L.L.P.

(57) ABSTRACT

A method for making microcapsules including an encapsulated material may include providing, in an aqueous continuous phase, one or more microcapsules including an encapsulated material surrounded by an inner shell including a first cross-linked polymer matrix. An outer surface of the inner shell may be hydrophobic. The method may also include adding thereto a polymerizable liquid component and a stabilizing agent, wherein the polymerizable liquid component is immiscible in the aqueous environment. The method may also include forming microcapsules wetted by the polymerizable liquid component. The method may further include polymerizing the polymerizable liquid component forming an outer shell including a second cross-linked polymer matrix formed about the inner shell. The microcapsules may be included in articles and compositions.

19 Claims, No Drawings

(56) References Cited

FOREIGN PATENT DOCUMENTS

| | | |
|---|---|---|
| GB | 989264 | 2/1966 |
| GB | 2 107 480 A | 4/1983 |
| JP | 58-182644 A | 10/1983 |
| WO | WO 02-060573 A2 | 8/2002 |
| WO | WO 2009-063257 A2 | 5/2009 |
| WO | WO 2011-117727 A1 | 9/2011 |
| WO | WO 2011-162944 A1 | 12/2011 |
| WO | WO 2013-182855 A2 | 12/2013 |

OTHER PUBLICATIONS

Search Report dated Oct. 24, 2012, for related GB Application No. GB 1211142.3.

* cited by examiner

MICROCAPSULES

CLAIM FOR PRIORITY

This application is a U.S. national phase entry under 35 U.S.C. § 371 from PCT International Application No. PCT/GB2013/051504, filed Jun. 7, 2013, which claims the benefit of priority of European Patent Application Nos. 1210156.4, filed Jun. 8, 2012, and 1211142.3, filed Jun. 22, 2012, the subject matter of all of which is incorporated herein by reference.

TECHNICAL FIELD

The present invention is directed to a method for making microcapsules comprising an encapsulated material, to microcapsules obtainable by that method, and to articles and compositions comprising said microcapsules.

BACKGROUND

The use of microcapsules is becoming increasingly common as a method for protecting and controlling the release of active ingredients. Microcapsules are used in a number of industries including agrochemicals, detergents, personal care products and pharmaceuticals. Core-shell capsules, in which droplets of the liquid active ingredient or solution are surrounded by a solid spherical shell, usually made of a polymer, can be prepared by a process of interfacial polymerization at the surface of the droplet. In this process, an emulsion (normally of the oil-in-water type, in which the active is present in the oil phase) is made, and the polymer shell is grown around the outside of the droplets.

There are many different types of chemical reactions that can be used for this process, and of these two have become common commercially. In the first, a di- or polyfunctional isocyanate compound is dissolved into the oil phase, and this solution is then emulsified under high shear conditions using a surfactant, water soluble polymer or 'protective colloid' to stabilize the droplets that are formed. The isocyanate then either reacts with the surrounding water to form a polyurea polymer at the droplet surface—a process that is relatively slow and requires heating and/or the use of a catalyst—or a water-soluble second reactant such as an amine or a polyfunctional alcohol is added to the water which reacts with the isocyanate to form a polyurea or polyurethane polymer respectively. Examples of these processes can be found in U.S. Pat. No. 3,577,515 and U.S. Pat. No. 4,285,720.

In the second commonly-used chemistry, the capsule wall is formed by the condensation of an amine (such as urea or melamine) or a phenolic compound with formaldehyde. This process was first described in the 1960s (see for example GB989264). All of the components are soluble in water, but the polymerization process is preferentially initiated on the surface of the emulsified droplets. Whilst this is a successful method of producing capsules, it can be difficult to remove traces of formaldehyde from the products, which can be undesirable.

Double-walled capsules with a polyurea inner shell and a urea-formaldehyde outer shell have been reported recently by different authors (Gang Li et al, *Polymer Bulletin* 60, 725-731 (2008); Caruso, M. M. et al, *Applied Materials and Interfaces* 2, (4), 1195-1199 (2010)). As with conventional urea-formaldehyde capsules, these rely on the tendency for urea-formaldehyde condensation to nucleate on the surface of the droplets or capsules. However, as mentioned above, it is generally desirable to avoid the use of formaldehyde.

WO-A-2009/063257 describes a process in which the surfactant used to stabilize an emulsion prior to the formation of microcapsules is replaced by mineral particles, so that a 'Pickering' emulsion is formed in which the particles are located at the oil/water interface. The examples within it describe the formation of capsules using an oil phase containing a polyisocyanate as the first reactant, and either an amine, an alcohol or water as the second reactant to form the capsule wall. The mineral particles become embedded in the polymer shell as polymerization proceeds. Such capsules have advantages over surfactant-stabilised, polymer-only capsules:

The use of mineral particles leads to a narrower size distribution emulsion which is also resistant to Ostwald ripening, a process in which the small solubility of the oil in water allows it to transfer between droplets, causing large droplets to grow and small droplets to shrink.

The size of the droplets can be controlled to a certain extent by the amount of mineral particles added.

The interior of the capsules is protected from ultraviolet degradation by light scattering from the particles in the shell.

The capsules can be dried without sticking or coalescing with each other.

The primary field of interest in WO-A-2009/063257 is the encapsulation of agrochemicals. It would advantageous to apply this technology to other applications outside of the field of interest of agrochemicals. One such application is the encapsulation of fragrance ingredients in detergents and personal care products. Such products are typically encapsulated commercially using the urea/melamine formaldehyde process described above.

Whilst some fragrances can be incorporated into leak-resistant capsules using the process described in WO-A-2009/063257, there are a number of 'difficult to encapsulate' formulations in which the leakage rate from the capsules in either alcohol or surfactant solutions is unacceptably high. Intact capsules are observed to form around these formulations, but it is believed that the capsule shells are too permeable to the core material in order to be effective. A method is therefore required by which the microcapsules can be made less permeable to a wider range of core ingredients.

SUMMARY OF THE INVENTION

According to a first aspect of the present invention, there is provided a method for making microcapsules comprising an encapsulated material, said method comprising: (a) providing, in an aqueous continuous phase, one or more microcapsules comprising an encapsulated material surrounded by an inner shell comprising a first cross-linked polymer matrix, wherein an outer surface of the inner shell is hydrophobic; (b) adding thereto a polymerizable liquid component and a stabilizing agent, wherein the polymerizable liquid component is immiscible in the aqueous environment, and forming microcapsules wetted by the polymerizable liquid component; and (c) polymerizing the polymerizable liquid component forming an outer shell comprising a second cross-linked polymer matrix formed about the inner shell.

According to a second aspect of the present invention, there is provided a microcapsule or microcapsules comprising an encapsulated material surrounded by an inner shell and an outer shell formed about the inner shell. The inner shell comprises a first cross-linked polymer matrix and the outer shell comprises a second cross-linked polymer matrix.

The microcapsule or microcapsules are obtainable by the method of the first aspect of the present invention.

According to a third aspect of the present invention, there is provided a microcapsule or microcapsules comprising an encapsulated material surrounded by an inner shell and an outer shell formed about the inner shell. The inner shell comprises a first cross-linked polymer matrix and the outer shell comprises a second cross-linked polymer matrix.

According to a fourth aspect of the present invention, there is provided an article of composition comprising microcapsules according to the second or third aspects of the present invention.

DETAILED DESCRIPTION

As used herein the term "shell" means a substantially continuous wall of cross-linked polymeric material formed about the encapsulated material or inner shell.

As used herein the terms "inner" and "outer" (shell) mean that the polymeric materials comprised in each shell are formed in distinct polymerization stages. In certain embodiments, for example, embodiments in which the first and second polymeric materials are of the same type (e.g., polyurethane), there may not be a distinct boundary between an inner and outer shell; that is to say, the boundary between an inner shell and outer shell may not be optically discernable (e.g., using scanning electron microscopy). In certain embodiments, there is an optically discernable (e.g., using scanning electron microscopy) boundary between the inner and outer shell.

As used herein the terms 'first' and 'second' with reference to various components, for example, inorganic particulate material or polymerizable liquid component or stabilizing agent, are used solely to differentiate between different components, and the use of such terms should not be taken to mean or imply that a moiety comprising a first component necessarily also includes a second component of the same genus or species.

As used herein the term 'formaldehyde-free' means that in certain embodiments the microcapsule(s) of the present invention are formed by methods which do not utilize or involve formaldehyde.

Unless otherwise stated, particle size properties referred to herein for the inorganic particulate materials are as measured in a well known manner by sedimentation of the particulate material in a fully dispersed condition in an aqueous medium using a Sedigraph 5100 machine as supplied by Micromeritics Instruments Corporation, Norcross, Ga., USA (web-site: www.micromeritics.com), referred to herein as a "Micromeritics Sedigraph 5100 unit". Such a machine provides measurements and a plot of the cumulative percentage by weight of particles having a size, referred to in the art as the 'equivalent spherical diameter' (e.s.d), less than given e.s.d values. The mean particle size $d_{50}$ is the value determined in this way of the particle e.s.d at which there are 50% by weight of the particles which have an equivalent spherical diameter less than that $d_{50}$ value. Similarly, $d_{90}$ is the value determined in this way of the particle e.s.d at which there are 90% by weight of the particulate which have an equivalent spherical diameter less than the $d_{90}$ value.

Alternatively, where stated, the particle size properties referred to herein for the microcapsules are as measured by the well known conventional method employed in the art of laser light scattering, using a Malvern Mastersizer S machine as supplied by Malvern Instruments Ltd (or by other methods which give essentially the same result). In the laser light scattering technique, the size of particles in powders, suspensions and emulsions may be measured using the diffraction of a laser beam, based on an application of Mie or Fraunhofer theory. Such a machine provides measurements and a plot of the cumulative percentage by volume of particles having a size, referred to in the art as the 'equivalent spherical diameter' (e.s.d), less than given e.s.d values. The mean particle size $d_{50}$ is the value determined in this way of the particle e.s.d at which there are 50% by volume of the particles which have an equivalent spherical diameter less than that $d_{50}$ value. Similarly, $d_{90}$ is the value determined in this way of the particle e.s.d at which there are 90% by volume of the particulate which have an equivalent spherical diameter less than the $d_{90}$ value.

In accordance with the first aspect of the present invention, the method comprises providing, in an aqueous continuous phase, one or more microcapsules comprising an encapsulated material surrounded by an inner shell comprising a first cross-linked polymer matrix. The outer surface of the inner shell is hydrophobic. Processes for preparing microcapsules comprising an encapsulated material surrounded by a single shell comprising a first cross-linked polymer matrix are provided below.

The aqueous continuous phase mostly comprises water, for example, by weight it is at least about 80% water, for example, at least about 90% water. The aqueous phase may comprise water miscible solvents.

The outer surface of the inner shell is hydrophobic to enable an outer shell, which is a substantially continuous wall comprising the second cross-linked polymer matrix, to be formed about the inner shell of the microcapsule provided in part (a) of the first aspect of the present invention. For the avoidance of doubt, the term "inner" used to describe the shell of the microcapsule provided in part (a) is used solely for the purpose of distinguishing the shell from the further (outer) shell which is formed about the shell of the microcapsule provided in part (a). In this respect, the present inventors have found that the interfacial polymerization technique in which the reactants are present in different phases is a self-limiting process; as the polymer shell forms between the two phases it eventually prevents mixing of the reactants at the interface and, thus, stops the reaction. The thickness of the shell is therefore limited by its permeability to the reactants, and it cannot be thickened simply by adding a higher concentration of a polymerizable liquid component, e.g., polyisocyanate, to the oil phase and increasing the amount of amine or alcohol added to the emulsion to form the polymer shell. For example, in Example 4 of WO-2009/063257 (see also Example 3 below), attempts were made to synthesise a 'two-layered capsule (see also Example 3 below), but this method is seen to lead to the formation of spheres which adhere to the outside of the single-wall capsule, rather than a substantially continuous wall about the inner shell. The present inventors have found that to grow further shells it is necessary to be able to add further reactants to the water phase, and for them to react at the capsule surface rather than in solution. This is achieved by hydrophobising an outer surface of the inner shell which changes the surface energy of the singled-walled microcapsule to allow it to be preferentially wetted by a water-immiscible polymerizable liquid component, which is then polymerized about the inner shell.

In certain embodiments, the outer surface of the inner shell is rendered hydrophobic by addition of a surfactant, for example, a cationic surfactant, such as those described below. The surfactant may be added as an aqueous solution, for example, a 5% by weight or less solution of surfactant, or 2% by weight or less solution, or 1% by weight or less solution of surfactant. In an embodiment, the surfactant is a quaternary ammonium salt having a hydrophobic tail, for example, di(hydrogenated tallow)dimethylammonium chloride.

In certain embodiments, addition of the surfactant to the outer surface of the inner shell is enhanced by provision, on the outer surface of the inner shell, of pendant moieties which become negatively charged under basic conditions, or positively charged under acidic conditions. The pendant groups may comprise acid groups, such as unsaturated or saturated carboxylic acid groups, or basic groups such as amino groups. In an advantageous embodiment, the pendant moieties are chemically bonded to one or more of the cross-linking agents used in the formation of the inner shell of the microcapsule provided in (a). Thus, in certain embodiments in which the pH of the aqueous environment during addition of a cationic surfactant is raised to render the pendant moieties negatively charged, the cationic head group of the surfactant becomes 'anchored' to the negatively charged pendant moieties. In these embodiments, the pH of the aqueous environment during addition of the surfactant may be equal to or greater than 8, for example, equal to or greater than 9, or equal or greater than about 10, or equal to or greater than about 11, or equal to or greater than about 12. The pH may be raised by the addition of an alkaline solution, for example, an alkali or alkali metal hydroxide, such as sodium or potassium hydroxide, or ammonium hydroxide. Typically, the basic solution will be stirred vigorously during addition of the surfactant. In alternative embodiments, the pH of the aqueous environment during addition of anionic or amphoteric surfactant is lowered to render the pendant moieties positively charged, so the anionic head group of the surfactant becomes 'anchored' to the positively charged pendant moieties. Hydrophobization of the outer surface of the inner shell will have a tendency to cause flocculation of the microcapsules.

The polymerizable liquid component added in (b) is immiscible in the aqueous environment. As discussed above, the polymerizable liquid component preferentially wets the surface of the hydrophobic inner shell of the microcapsule. This may cause the wetted microcapsules to begin to, partially, or fully phase separate. Because the hydrophobic microcapsules have a tendency to flocculate and/or phase separate, a stabilizing agent is added along with the polymerizable liquid component.

The stabilizing agent serves to enhance the stability of an emulsion and to reduce or suppress the tendency of the oily droplets or single-shell microcapsules to flocculate or phase separate over time.

The stabilizing agent may be a surfactant or a surface-modified inorganic particulate material or a combination thereof.

Suitable surfactants may be anionic, cationic, non-ionic or amphoteric.

Exemplary anionic surfactants include: sulfates, such as alkyl sulfates (e.g., ammonium lauryl sulfate and sodium lauryl sulfate) and alkyl ether sulfates (e.g., sodium laureth sulfate and sodium myreth sulfate); sulfonates, such as docusates (e.g., dioctyl sodium sulfosuccinate), sulfonate fluorosurfactants (e.g., perfluorooctanesulfonate and perfluorobutanesulfonate) and alkyl benzene sulfonates; phosphates, such as alkyl aryl ether phosphate and alkyl ether phosphate; carboxylates, such as alkyl carboxylates, (e.g., fatty acid salts such as sodium stearate), sodium lauroyl sarcinoate, and carboxy fluorosurfactants (e.g., perfluorononanoate and perfluorooctanoate).

Exemplary cationic surfactants include primary, secondary, or tertiary amines, such as octenidine dihydrochloride; quaternary ammonium salts having a hydrophobic tail, such as di(hydrogenated tallow)dimethylammonium chloride, alkyltrimethylammonium salts, such as cetyl trimethylammonium bromide and cetyl trimethylammonium chloride; or one or more of cetylpyridinium chloride, benzalkonium chloride, benzethonium chloride, 5-bromo-5-nitro-1,3-dioxane, dimethyldioctadecylammonium chloride, and dioctadecyldimethylammonium bromide.

Exemplary amphoteric surfactants include (3-[(3-cholamidopropyl)dimethylammonio]-1-propanesulfonate); cocamidopropyl hydroxysultaine, amino acids, imino acids, cocamidopropyl betaine and lecithin.

Exemplary non-ionic surfactants include fatty alcohols, such as cetyl alcohol, stearyl alcohol, cetostearyl alcohol (consisting predominantly of cetyl and stearyl alcohols) and oleyl alcohol; polyoxyethylene glycol alkyl ethers (i.e., moieties of the general formula $CH_3$—$(CH_2)_{10-16}$—(O—$C_2H_4)_{1-25}$—OH, such as octaethylene glycol monododecyl ether and pentaethylene glycol monododecyl ether; polyoxypropylene glycol alkyl ethers of the general formula $CH_3$—$(CH_2)_{10-16}$—(O—$C_3H_6)_{1-25}$—OH; glucoside alkyl ethers, such as decyl glucoside, lauryl glucoside and octyl glucoside; polyoxyethylene glycol octylphenol ethers of the general formula $C_8H_{17}$—$(C_6H_4)$—(O—$C_2H_4)_{1-25}$—OH; polyoxyethylene glycol alkylphenol ethers of the general formula $C_9H_{19}$—$(C_6H_4)$—(O—$C_2H_4)_{1-25}$—OH; glycerol alkyl esters, such as glyceryl laurate; polyoxyethylene glycol sorbitan alkyl esters, such as polysorbate; sorbitan alkyl esters; cocamide MEA or cocamide DEA; dodecyldimethylamine oxide; block copolymers of polyethylene glycol and polypropylene glycol; and polyethoxylated tallow amine.

Exemplary inorganic particulate material includes silica, silicates, marble, clays and talc. Inorganic particulate materials may be naturally occurring or synthetic. In certain embodiments, the inorganic particulate material is selected from the group consisting of kaolin, bentonite, alumina, limestone, bauxite, gypsum, magnesium carbonate, calcium carbonate (ground and/or precipitated), perlite, dolomite, diatomite, huntite, magnesite, boehmite, palygorskite, mica, vermiculite, hydrotalcite, hectorite, hallyosite, gibbsite, kaolinite, montmorillonite, illite, attapulgite, laponite and sepiolite, and combinations thereof.

In advantageous embodiments, the inorganic particulate material is kaolin (clay). Kaolin clay is also referred to as china clay or hydrous kaolin, and is predominantly mineral kaolinite ($Al_2(Si_2O_5)(OH)_4$), a hydrous aluminosilicate.

In certain embodiments, the inorganic particulate material has a $d_{50}$ of equal to or less than about 10 μm. For example, the inorganic particulate may have a $d_{50}$ of equal to or less than about 5 μm, or equal to or less than about 2 μm, or equal to or less than about 1 μm, or equal to or less than about 0.9 μm, or equal to or less than about 0.8 μm, or equal to or less than about 0.7 μm, or equal to or less than about 0.6 μm, or equal to or less than about 0.5 μm, or equal to or less than about 0.4 μm, or equal to or less than about 0.3 μm. Advantageously, the inorganic particulate material may have $d_{50}$ of equal to or less than about 0.2 μm, for example, equal to or less than about 0.18 μm, or equal to or less than about 0.15 μm, or equal to or less than about 0.12 μm, or equal to or less than about 0.10 μm. In certain embodiments, the $d_{50}$ of the inorganic particulate material is greater than about 0.025 μm, for example, greater than about 0.05 μm.

In further embodiments, the inorganic particulate material has a particle size distribution such that at least about 90% by weight of the particles are smaller than about 2 μm, i.e., a $d_{90}$ of less than about 2 µm, for example, at least about 95% by weight, or at least 98% by weight of the particles are smaller than about 2 µm. The inorganic particulate material may have a $d_{90}$ of less than about 1 µm, for example, at least about 95% by weight, or at least about 98% by weight of the particles are smaller than about 1 µm. In further embodiments, at least about 75% by weight of the particles are smaller than about 0.25 µm, for example, at least about 80% by weight, or at least about 82% by weight of the particles are smaller than about 0.25 µm.

Surface modified means that the inorganic particle surface has been (chemically) modified so to have reactive functional groups which, in certain embodiments, may be cross-linkable with a polymerizable liquid component. The surface of the particles may be modified using modifying agents having the general structure X-Y-Z, in which X is a chemical moiety with an affinity for the particle surface. Z is a reactive chemical moiety with a desired functionality, and Y is a chemical moiety that links X and Z together. The term "affinity" relates to chemical moieties that are either chemically bonded or physisorbed to the particle surface. Advantageously, they are chemically bonded.

X may be, for example, an alkoxy silane group such as tri-ethoxysilane or tri-methoxy silane, which is particularly useful when the particles have silanol (SiOH) groups on their surface. X may also be, for example, an acid group (such as a carboxylic acid or an acrylic acid group) which is particularly useful when the particles have basic groups on their surface.

Y may be any chemical group that links X and Z together, for example, a polyamide, a polyester, or an alkylene chain. Advantageously, Y is an alkylene chain, for example, a $C_{2-6}$ alkylene chain, such as ethylene, propylene or butylene.

Z may be, for example, an epoxy group, a carboxylic acid group, an unsaturated hydrocarbon such as acrylic or vinyl, or an amine group. Advantageously. Z is an amine. As noted above, in particular embodiments, Z is of form which is suitable to cross-link with the polymerizable liquid component to form the polymer matrix of the inner and/or outer shell of the microcapsules according to embodiments of the present invention.

Exemplary surface modifying agents may be selected from trimethoxysilyl ethyl amine, triethoxysilyl ethyl amine, tripropoxysilyl ethyl amine, tributoxysilyl ethyl amine, trimethoxysilyl propyl amine, triethoxysilyl propyl amine, tripropoxysilyl propyl amine, triisopropoxysilyl propyl amine, tributoxysilyl propyl amine, trimethoxysilyl butyl amine, triethoxysilyl butyl amine, tripropoxysilyl butyl amine, tributoxysilyl butyl amine, trimethoxysilyl pentyl amine, triethoxysilyl pentyl amine, tripropoxysilyl pentyl amine, tributoxysilyl pentyl amine, trimethoxysilyl hexyl amine, triethoxysilyl hexyl amine, tripropoxysilyl hexyl amine, tributoxysilyl hexyl amine, trimethoxysilyl heptyl amine, triethoxysilyl heptyl amine, tripropoxysilyl heptyl amine, tributoxysilyl heptyl amine, trimethoxysilyl octyl amine, triethoxysilyl octyl amine, tripropoxysilyl octyl amine, tributoxysilyl octyl amine, and mixtures thereof.

In advantageous embodiments, the surface modify agent is triethoxysilyl propyl amine.

In one embodiment, the inorganic particulate material, for example, kaolin clay, is reacted with a suitable surface modifying agent, in the range of from about 0.1 to about 30% of the modifying molecule based on the weight of the kaolin clay, for example, in the range of from about 0.1 to about 20%, or from about 0.1 to about 10% by weight.

The addition of a surface-modified inorganic particulate material leads to the formation of a Pickering emulsion, which stabilizes the wetted microcapsules which are surrounded by the particles of the inorganic particulate material.

The weight ratio of surface-modified inorganic particulate material to single-walled microcapsules in the aqueous continuous phase will be from about 1:1 to about 1:40, for example, from about 1:5 to about 1:30, for example, from about 1:10 to about 1:20.

Owing to flocculation of the hydrophobic microcapsules, the emulsion may be vigorously agitated, e.g., sheared, during (b), e.g., during addition of the stabilizing agent. Agitation/shearing may be conducted by conventional means such as ultrasonic dispersers, or high speed mechanical mixers such as Rotor/stator mixer, Ystral® or Ultra Turrax®. Agitation/shearing may be carried for a period of time sufficient to re-disperse the wetter microcapsules. For example, the high speed mechanical mixer may be operated at a speed of at least about 5000 rpm, for example, at least about 10,000 rpm, or at least about 15,000 rpm, or equal to or greater than about 20,000 rpm, for a period of up to about 60 minutes, or up to about 30 minutes, or up to about 20 minutes, or up to about 10 minutes, or for about 9 minutes, or about 8 minutes, or about 7 minutes, or about 6 minutes, or about 5 minutes, or about 4 minutes, or about 3 minutes, or about 2 minutes. In certain embodiments, the period of time is at least about 30 seconds, for example, at least about 1 minute.

In accordance with (c) of the first aspect of the present invention, the polymerizable liquid component is polymerized forming an outer shell comprising a second cross-linked polymer matrix formed about the inner shell.

In embodiments, the polymerizable liquid component is of a form suitable to form the second cross-linked polymer matrix upon polymerization in the presence of a cross-linking agent which is soluble in the aqueous environment. In an embodiment, the second cross-linked polymer matrix is selected from polyurethane, polyurea, polyepoxide, polyamide, polyester, polysulfonamide, polycarbonate and combinations thereof, and a person of skill in the art will be able to select a combination of polymerizable liquid component and cross-linking agent to form a second cross-linked polymer matrix of the types described above. The cross-linking agent may be the water of the aqueous continuous phase. For example, if the polymerizable liquid component is an isocyanate, it can be left to polymerize with the surrounding water to form a polyurea polymer. This process is relatively slow and typically requires heating and/or the use of a polymerization catalyst, such as 1,4-diazabicyclo[2.2.2]octane.

In embodiments in which the second cross-linked polymer matrix is a polyurea, the polymerizable liquid component may be an isocyanate and the cross-linking agent may be a water soluble amine, for example, a di- or polyfunctional amine. The isocyanate may be a polyisocyanate, for example, an aromatic polyisocyanate, including aromatic diisocyanates, an aliphatic polyisocyanate, including aliphatic diisocyanates, or a high molecular weight linear aliphatic diisocyanate. The isocyanate may be an isocyanate pre-polymer. Exemplary isocyanates include 1-chloro-2,4-phenyl dissocynate, m-phenylene dissocyanate, p-phenyl diisocyanate, 4,4'-methylenebis (phenyl isocyanate), 4,4'-methylenebis (2-methylphenyl isocyanate), 2,4-tolylene dissocyanate, 2,6-tolylene diisocyanate, 3,3-dimethyl-4,4'-biphenyl diisocyanate, 3,3'-dimethoxy-4,4'-biphenylene dissocyanate, 2,2',5,5'-tetramethyl-4,4'biphenylene dissocyanante, and polymethylene polyphenylene diisocyanate. In an advantageous embodiment, the water-immiscible polymerizable liquid component is a polyisocyanate, for example, polymethylene polyphenylene diisocyanate. In other embodiments in which the second-cross-linked polymer matrix is a polyurea, the water-immiscible polymerizable component may be phosgene (chloroformyl chloride).

Exemplary di- and polyfunctional amines include ethylene diamine, phenylene diamine, toluene diamine, hexamethylene diamine, diethylenetriamine, piperazine, 1,3,5-benzene triamine trihydrochloride, 2,4,6-triamino toluene trihydrochloride, tetraethylene pentaamine, pentaethylene hexamine, polyethylene imine, 1,3,6 triaminonaphthalene, 3,4,5 triamino-1,2,4 triazole melamine and 1,4,5,8 tetramino anthraquinone.

In certain embodiments, the amine is a di- or triamine.

In embodiments in which the second cross-linked polymer matrix is a polyurethane, the polymerizable component may be an isocyanate, including any of the isocyanate species described above, advantageously a polyisocyanate, and the cross-linking agent may be a water soluble alcohol, for example a diol or polyol. In an advantageous embodiment, the diol or polyol has an acid group, for example, a carboxylic acid, such as methanoic acid, ethanoic acid, propanoic acid or butanoic acid.

Exemplary diols include bisphenol A [(2,2 bis (p,p' dihydroxy diphenyl) propane], hydroquinone, resorcinol, catechol, ethylene glycol, pentanediol, hexanediol, and dodecanediol, and 2,2-Bis(hydroxymethyl) propionic acid). Exemplary polyols include 1,2,3-benzene-triol, phloroglucinol dehydrate, pentaerythritol, trimethylolpropane, 1,4,9,10 tetrahydroxyanthracene, 3,4 dihydroxyanthranol, diresorcinol, tetrahydroxy quinine and anthralin.

In certain embodiments, the alcohol is a diol.

In other embodiments in which the second cross-linked polymer matrix is a polyurethane, the polymerizable liquid component may be a bischloroformate or polychloroformate and the cross-linking agent may be a di- or polyfunctional amine, including any of the di- and polyfunctional amine species described above.

In certain embodiments in which the second cross-linked polymer matrix is a polyamide, the polymerizable liquid component may be a diacid or polyacid, for example, a di- or polycarboxylic acid, or a di- or polycarboxylic acid chloride, and the cross-linking agent may be an amine, for example, a di- or polyfunctional amine, including any of the di- or polyfunctional amine species described above.

Exemplary diacids and polyacids include hexanedioic acid, heptanedioic acid, octanedioic acid, nonanedioic acid, decanedioic acid, undecanedioic acid, dodecanedioic acid, benzene-1,2-dicarboxylic acid, benzene-1,3-dicarboxylic acid, or benzene-1,4-dicarboxylic acid. Exemplary acid chlorides include sebacoyl chloride, adipoyl chloride, terepthaloyl chloride, azelaoyl chloride and dodecanedioic acid chloride. Acid chlorides may be dissolved in a suitable solvent as required.

In certain embodiments in which the second cross-linked polymer matrix is a polyepoxide, the polymerizable liquid component may be a glycidyl ether, such as bisphenol A diglycidyl ether, and the cross-linking agent may be an amine, for example, a di- or polyfunctional amine, including any of the di- or polyfunctional amine species described above, or any other suitable cross-linking agent.

In certain embodiments in which the second cross-linked polymer matrix is a polyester, the polymerizable liquid component may be a carboxylic acid or acid chloride, and the cross-linking agent may be a diol or polyol, including any of the diol or polyol species described above.

In certain embodiments in which the second cross-linked polymer matrix is a polysulfonamide, the polymerizable liquid component may be a di- or polysulfonyl chloride, and the cross-linking agent may be amine, for example, a di- or polyfunctional amine, including any of the di- or polyfunctional amine species described above.

In certain embodiments in which the second-cross-linked polymer is a polycarbonate, the polymerizable component may be a bischloroformate, polychloroformate or phosgene, and the cross-linking agent may be a diol or polyol, including any of the of the diol and polyol species described above.

In an advantageous embodiment, the method of the first aspect of the presence invention does not utilise or involve formaldehyde.

During polymerization the mixture may be stirred. The mixture may be heated and a polymerization catalyst may be included if desired. Suitable amounts of polymerizable liquid component and cross-lining agents are added to enable the formation of the outer shell about the inner shell. The weight ratio of polymerizable liquid component to cross-linking agent may be in the range of from about 20:1 to about 1:20, for example, from about 10:1 to about 1:10, or from about 5:1 to about 1:5. The cross-linking agent may be added in the form of an aqueous solution comprising from about 5% by weight to about 50% by weight of the cross-linking agent.

In certain embodiments, the encapsulated material is a liquid which is substantially insoluble in water, for example, a liquid having a solubility in water at 20° C. of less than about 10 g/l, or less than about 5 g/l, or less than about 2 g/l, or less than about 1 g/l. The encapsulated material may comprise, consist essentially or consist of an active agent. The active agent may be provided in a solvent, particularly if at room temperature (e.g., between about 15° C. and 25° C.) it is a solid, or highly viscous. Thus, the active agent may be the liquid, a part of the liquid, dissolved in the liquid or dispersed in the liquid. The active agent may be less than about 1% by weight soluble in water, for example, less than about 0.1% by weight soluble in water.

A wide range of active agents may be encapsulated, including fragrances, perfumes, cosmetics, sunscreens, active agents that are included in detergents, fabric softeners, and other household cleaning products (such as bleaches, enzymes and surfactants), inks, flavours, food additives other than flavours, adhesives, sealants, phase change materials, biocides, oilfield chemicals (including corrosion and scale inhibitors), flame retardants, active agents that are included in textiles (such as insect repellents, antimicrobial agents, skin softeners and medically active compounds), active agents that may be included in coatings (such as fire retardant, flame retardant, antifouling, antibacterial biocidal, scratch resistant and abrasion resistant compounds, biologically active compounds, pharmaceutically active compounds, and agrochemicals (such as herbicides, fungicides or insecticides).

In certain embodiments, the active agent is a fragrance, for example, fragrances of the type that are used in perfumes, colognes, personal care products (such as shampoos, hair conditions, soaps, gels) or household products, such as cleaners (e.g., to mask the smell of cleaning chemicals) or air fresheners.

The fragrance may comprise or consist of fragrance oil. Typically, but not exclusively, a fragrance oil is a complex blend or mixture of synthetic/natural aroma compounds or natural essential oils, that may be diluted with a carrier fluid, such as propylene glycol, vegetable oil or mineral oil. An aroma compound is a chemical compound that has a smell or odour. Aroma compounds include, but are not limited to, esters, aldehydes, ketones, linear and cyclic terpenes, aromatics, alcohols, lactones, thiols, and the like. Exemplary esters include geranyl acetate, methyl formate, methyl acetate, methyl butyrate, ethyl acetate, ethyl butyrate, isoamyl acetate, pentyl butyrate, pentyl pentanoate, octyl acetate, fructone, hexyl acetate and ethyl methylphenylglycidate. Exemplary linear terpenes include myrcene, geraniol, nerol, citral, citronellal, citronellol, linalool and nerolidol. Exemplary cyclic terpenes include limonene, camphor, terpineol, alpha-Ionone and thujone. Exemplary aromatics include benzaldehyde, eugenol, cinnamaldehyde, ethyl maltol, vanillin, anisole, anethole, estragole and thymol. Exemplary alcohols include furaneol, 1-hexanol, cis-3-Hexen-1-ol and menthol. Exemplary aldehydes include acetaldehyde, hexanal, cis-3-hexanal, furfural and hexyl cinnamaldehyde. Exemplary ketones include dihydrojasmone, oct-1-en-3-one, 2-acetly-1-pyrroline and 6-acetly-2,3,4,5-tetrahydropyridine. Exemplary lactones include γ-decalactone, γ-nonalactone, δ-octalactone, jasmine lactone, mossoia lactone, wine lactone and sotolon. Exemplary thiols include ethanethiol, 2-methyl-2-propanethiol, butane-1-thiol, grapefruit mercaptan and methanethiol.

The single-shell microcapsule provided in part (a) of the first aspect of the present invention may be prepared using any suitable method including, but not limited to, the methods described in WO-A-2009/063257, the entire contents of which are hereby incorporated by reference.

In certain embodiments, the microcapsule provided in (a) is prepared by a process comprising:
 i. forming an emulsion of material to be encapsulated (as described above) in an aqueous environment, optionally in the presence of a stabilizing agent, wherein said material to be encapsulated comprises a polymerizable liquid component which is immiscible in the aqueous environment; and
 ii. forming said inner shell comprising a first cross-linked polymer matrix by interfacial polymerization of said polymerizable liquid component with a cross-linking agent.

The material to be encapsulated, as described above, must dissolve the polymerizable liquid component used to prepare first cross-linked polymer matrix comprised in the inner shell.

The stabilizing agent, when present, may be selected from a surfactant, a surface-modified inorganic particulate material, and a combination thereof. Suitable surfactants and surface modified inorganic particulate materials are described above. In certain embodiments, the stabilizing agent, for example, a surface-modified inorganic particulate material, used in the preparation of the single-shell microcapsule and the double-shell microcapsules of the present invention are of the same form. If the surface-modified inorganic particulate comprises polymerizable cross-linking groups, i.e., if reactive chemical moiety Z is a cross-linking agent, these may participate in the polymerization of the polymerizable liquid component. As described above, the addition of a surface-modified inorganic particulate material leads to the formation of a Pickering emulsion, which stabilizes the emulsified droplets of material to be encapsulated.

The first cross-linked polymer matrix may be selected from polyurethane, polyurea, polyepoxide, polyamide, polyester, polysulfonamide, polycarbonate and a person of skill in the art will be able to select a combination of polymerizable liquid component and cross-linking agent to form a second cross-linked polymer matrix of the types described above. The cross-linking agent may be the water of the aqueous continuous phase. For example, if the polymerizable liquid component is an isocyanate, it can be left to polymerize with the surrounding water to form a polyurea polymer. This process is relatively slow and typically requires heating and/or the use of a polymerization catalyst, such as 1,4-diazabicyclo[2.2.2]octane.

Any suitable combination of polymerizable liquid component and cross-linking agent as described above in relation to the methods for preparing the double-shell microcapsules of the present invention may be used to form the first cross-linked polymer matrix. In certain embodiments, the first cross-linked polymer matrix is a polyurea or polyurethane.

In certain embodiments the cross-linking agent is a water soluble alcohol, for example a diol or polyol. In an advantageous embodiment, the diol or polyol has an acid group, for example, a carboxylic acid, such as methanoic acid, ethanoic acid, propanoic acid or butanoic acid.

The emulsion may be formed by vigorously agitating the reactants, e.g., by shearing. Agitation/shearing may be conducted by conventional means such as ultrasonic dispersers, or high speed mechanical mixers such as Rotor/stator mixer, Ystral® or Ultra Turrax®. Agitation/shearing may be carried for a period of time sufficient to form an emulsion. For example, the high speed mechanical mixer may be operated at a speed of at least about 5000 rpm, for example, at least about 10,000 rpm, or at least about 15,000 rpm, or equal to or greater than about 20,000 rpm, for a period of up to about 60 minutes, or up to about 30 minutes, or up to about 20 minutes, or up to about 10 minutes, or for about 9 minutes, or about 8 minutes, or about 7 minutes, or about 6 minutes, or about 5 minutes, or about 4 minutes, or about 3 minutes, or about 2 minutes. In certain embodiments, the period of time is at least about 30 seconds, for example, at least about 1 minute.

In accordance with the second aspect of the present invention, there is provided a microcapsule or microcapsules comprising an encapsulated material surrounded by an inner shell and an outer shell formed about the inner shell, the inner shell comprising a first cross-linked polymer matrix, the outer shell comprising a second cross-linked polymer matrix, which is obtainable by a method according to the first aspect of the present invention.

In accordance with the third aspect of the present invention, there is provided a microcapsule or microcapsules comprising an encapsulated material surrounded by an inner shell and an outer shell formed about the inner shell, wherein the inner shell comprises a first cross-linked polymer matrix and the outer shell comprises a second cross-linked polymer matrix.

The inner shell may comprise an inorganic particulate material, or (ii) the outer shell may comprise an inorganic particulate material, or (iii) both the inner shell and outer shell comprise an inorganic particulate material. The inorganic particulate material is selected from one or more of the inorganic particulate materials described above and, if present, is incorporated in the inner and/or outer shell in the form of a surface modified inorganic particulate. Surface modifying agents include any of the surface modifying agents described above, including those having the general structure X-Y-Z, in which X is a chemical moiety with an affinity for the particle surface, Z is a reactive chemical moiety with a desired functionality, and Y is a chemical moiety that links X and Z together.

In advantageous embodiments the inorganic particulate material is kaolin.

In certain embodiments, the inorganic particulate material has a $d_{50}$ of equal to or less than about 10 µm. For example, the inorganic particulate may have a $d_{50}$ of equal to or less than about 5 µm, or equal to or less than about 2 µm, or equal to or less than about 1 µm, or equal to or less than about 0.9 µm, or equal to or less than about 0.8 µm, or equal to or less than about 0.7 µm, or equal to or less than about 0.6 µm, or equal to or less than about 0.5 µm, or equal to or less than about 0.4 µm, or equal to or less than about 0.3 µm. Advantageously, the inorganic particulate material may have $d_{50}$ of equal to or less than about 0.25 µm, for example, equal to or less than about 0.2 µm, or equal to or less than about 0.18 µm, or equal to or less than about 0.15 µm, or equal to or less than about 0.12 µm, or equal to or less than about 0.10 µm. In certain embodiments, the $d_{50}$ of the inorganic particulate material is greater than about 0.025 µm, for example, greater than about 0.05 µm. The inorganic particulate material may have a $d_{90}$ of equal to or less than about 20 µm, for example, equal to or less than about 15 µm, or equal to or less than about 10 µm, or equal to or less than about 5 µm, or equal to or less than about 3 µm, or equal to or less than about 2 µm, or equal to or less than about 1.5 µm, or equal to or less than about 0.5 µm.

In further embodiments, the inorganic particulate material has a particle size distribution such that at least about 90% by weight of the particles are small than about 2 µm, i.e., a $d_{90}$ of less than about 2 µm, for example, at least about 95% by weight, or at least 98% by weight of the particles are smaller than about 2 µm. The inorganic particulate material may have a $d_{90}$ of less than about 1 µm, for example, at least about 95% by weight, or at least about 98% by weight of the particles are smaller than about 1 µm. In further embodiments, at least about 75% by weight of the particles are smaller than about 0.25 µm, for example, at least about 80% by weight, or at least about 82% by weight of the particles are smaller than about 0.25 µm.

The first cross-linked polymer matrix and the second cross-linked polymer matrix may be selected, independently, from polyurethane, polyurea, polyepoxide, polyamide, polyester, polysulfonamide, polycarbonate, and combinations thereof.

In embodiments, the first cross-linked polymer matrix is polyurethane or polyurea. In another embodiment, the second cross-linked polymer is selected from polyurethane, polyurea and polyepoxide. In another embodiment, the first cross-linked polymer matrix is polyurethane or polyurea and the second cross-linked polymer is selected from polyurethane, polyurea and polyepoxide.

The microcapsule or microcapsules according to the second or third aspects of the present invention may comprise one or more further shells comprising a cross-linked polymer matrix formed about the outer shell.

Suitable encapsulated materials are described above. In certain embodiments, the active agent is a fragrance, for example, fragrances of the type that are used in perfumes, colognes, personal care products (such as shampoos, hair conditioners, soaps, gels) or household products, such as cleaners (e.g., to mask the smell of cleaning chemicals) or air fresheners.

The microcapsules according to the second and third aspects of the present invention may have a $d_{50}$ (volume % by laser light scattering) of equal to or greater than about 20 µm, for example, equal to or greater than about 25, or equal to or greater than about 30 µm, or equal to or greater than about 35 µm, or equal to or greater than about 40 µm, or equal to or greater than about 41 µm, or equal to or greater than about 42 µm, or equal to or greater than about 43 µm, or equal to or greater than about 44 µm, or equal to or greater than about 45 µm, or equal to or greater than about 46 µm, or equal to or greater than about 47 µm, or equal to or greater than about 48 µm, or equal to or greater than about 49 µm, or equal to or greater than about 50 µm, or equal to or greater than about 55 µm, or equal to or greater than about 60 µm, or equal to or greater than about 65 µm, or equal to or greater than about 70 µm, or equal to or greater than about 75 µm, or equal to or greater than about 75 µm, or equal to or greater than about 80 µm. In certain embodiments, the microcapsules have a $d_{50}$ of less than about 250 µm, for example, less than about 225 µm, or less than about 200 µm, or less than about 180 µm, or less than about 160 µm, or less than about 140 µm, or less than about 120 µm, or less than about 100 µm.

In an embodiment, the $d_{50}$ of the microcapsules of the second and third aspects of the present invention is at least about 5% greater than the $d_{50}$ of the single-shell microcapsules provided in part (a) of the first aspect of the present invention, for example, at least about 10% greater, or at least about 15% greater, or at least about 20% greater, or at least about 25% greater In an advantageous embodiment, the microcapsules according to the second and third aspect of the present invention are formaldehyde-free.

The microcapsules of the present invention may be characterised by improved leakage rates, for example, a 24 hr leakage rate; that is to say the leakage rate of the encapsulated material. Thus, in an embodiment, the microcapsule or microcapsules of the second and third aspect of the present invention, having an inner shell and outer shell formed in distinct polymerization stages, have a leakage rate, for example, a 24 hour leakage rate, which is lower compared to (1) a microcapsule having only a single-shell prepared in accordance with steps (i) and (ii) of the first aspect of the present invention, or (2) a microcapsule having an inner shell prepared in accordance with (i) and (ii) of the first aspect of the present invention, wherein the outer surface of the inner shell is not hydrophobic, and which is subjected to a further polymerization step with a water-solvable polymerizable component, e.g., such as the method described in Example 4 of WO2009/063257. Leakage rate may be determined in accordance with the method described in the Examples below.

Thus, in an embodiment, the microcapsules of the present invention are used to suppress leakage of the material encapsulated therein.

In certain embodiments, the microcapsules according to the second and third aspects of the present invention may have a 24 hour leakage rate of less than about 60% of the encapsulate material, for example, less than about 55%, or less than about 50%, or less than about 45%, or less than about 40%, or less than about 35%, or less than about 30%, or less than about 25%, or less than about 20%, or less than about 15%, or less than about 10%.

In certain embodiments, the method of the first aspect of the present invention may further comprise drying, for example, spray drying, the microcapsules formed in (c).

In certain embodiments, the microcapsules are provided in the form of a dried powder.

Microcapsules according to the second and third aspects of the present invention may be incorporated in articles or compositions. Thus, in accordance with a fourth aspect there is provided an article or composition comprising microcapsules according to the second and third aspects of the present invention.

Compositions include detergents and personal care products, such as shampoos, hair conditioners, soaps and gels. For use in such compositions the encapsulated material may be fragrance. Provision of the fragrance in the microcapsules of the present invention may enable the capsule to be retained on a substrate (e.g., clothing, linen, hair, etc) after rinsing, and then the fragrance may be released by rupture of the capsules by mechanical abrasion after drying (e.g., drying with a towel). Further, the incorporation of inorganic particulate material into the inner and/or outer shell may also provide other benefits, including adhering the capsules to a substrate, and strengthening them so that they survive a washing stage and then undergo brittle fracture (rupture) after a drying stage.

Further suitable applications include:

Sustained release or controlled release usages, for example: pharma, for example acid resistant capsules (oral delivery past low pH in the stomach), protection of labile actives, pseudo-zero order release through capsule wall and Ostwald-ripening resistant emulsion formulations; cosmetics; perfumes, for example slowing down evaporation of top-notes or sustained release and minimising overpowering odours; capsules having affinity for cellulose and trapped on textile surface during laundering; flavours, for example light stabilised to prevent oxidation; self-healing coatings, for example capsule bursts to release a resin that repairs damage; carbonless copy paper; novel, double taste and texture food, for example capsule which dissolves in the mouth and releases a new taste; pressure sensitive adhesives; sealants; nutrition (for example increased bioavailability of complex molecules and protection of sensitive molecules such as vitamins, probiotics and other food additives); toner inks with photosensitivity or thermal sensitivity; textile coatings, for example, for improving permeability properties; anti-fouling coatings; surface protective coatings, for example, for improving scratch or abrasion resistance; and construction materials, for example wall-boards, plasterboards and cements. Example of capsules that are dried out, include, for example, various mineral blends to form a ceramic upon calcination; low density fillers for polymers or paints; insulating materials; low density proppants; light reinforcing particles, for example for wood-fibre composites; recyclable pigments, for example low density allowing easy flotation separation; and energy buffers, for example use in a void in spheres to provide a 'crash barrier' with adsorption of energy. Capsules of the present invention may be of novel size or shape, for example: creation of plate or rod shape capsules; and use of metallic particles resulting in conductive capsules, or having a metallic nature, for example plasmon absorbance.

The invention will now be illustrated, by reference to the following non-limiting examples.

EXAMPLES

Example 1

Polyurethane microcapsules containing a fragrance oil formulation consisting of a complex mixture of esters and ketones were first synthesised according to the following procedure, in the quantities shown in Table 1. A polyphenylene polymethylene isocyanate (Desmodur VLR20, Bayer) was dissolved into the fragrance oil at approximately 10 wt. % concentration. This was added to an aqueous suspension of 5 wt. % aminopropyltriethoxysilane-treated ultrafine kaolin having a $d_{50}$ of about 0.12 μm and a small amount of further water, and then sheared vigorously with an Ultra-Turrax homogeniser at 20,000 rpm for 2 minutes to form an emulsion.

TABLE 1

| | |
|---|---|
| Fragrance oil | 34.2 g |
| Desmodur VLR20 | 3.8 g |
| Aminosilane-treated kaolin (5 wt % in water) | 47.4 g |
| Water | 9.5 g |

After the high shear step the emulsion was then stirred gently with a paddle mixer, and heated to 70° C. over a period of 30 minutes. The droplets were encapsulated by forming a polyurethane shell upon addition of the ingredients in Table 2 and stirring at 70° C. for a period of 90 minutes. Analysis of these capsules by laser diffraction (Malvern Mastersizer S) showed them to have a median size of 38 μm.

TABLE 2

| | |
|---|---|
| 1,5 Pentanediol | 4.12 g |
| 2,2-Bis(hydroxymethyl) Propionic Acid (DMPA) - 25 wt % solution in water | 8.33 g |
| 1,4-diazabicyclo[2.2.2]octane (DABCO) - 20 wt % solution in water | 1.0 g |

A 1 g sample of the capsule suspension was then mixed with 3.75 g of isopropanol. Both the fragrance oil and the water are soluble in isopropanol, and this quantity was previously shown to be sufficient to form a single phase with 1 g of the unencapsulated emulsion. After shaking, the suspension was split into two parts. The first was filtered immediately and the filtrate analysed for fragrance concentration by UV spectroscopy, and the second was left for 24 hrs before filtration and analysis. The percentage of the fragrance that had leaked from the capsules in each sample was calculated, and is shown in Table 4.

A small amount of NaOH solution in water was then added to a 20 g sample of the single-walled capsules to raise its pH to 10, followed by an aqueous solution of di(hydrogenated tallow)dimethylammonium chloride (Arquad 2HT, Akzo Nobel) to render the capsules hydrophobic, and stirred vigorously. Flocculation of the capsules was observed. A further dose of the polyisocyanate was then added with stirring, causing the capsules to be wetted by it and to phase separate. Upon addition of further aminopropyltriethoxysilane-treated ultrafine kaolin and shearing with an ultra-turrax at 20,000 rpm the polyisocyanate-coated capsules became re-dispersed. A solution of diethylene tetramine (DETA) in water was then added with gentle stirring to polymerise the isocyanate and complete the second polyurea shell. Quantities used are shown in Table 3.

TABLE 3

| | |
|---|---|
| Single-Walled Capsule suspension | 20.0 g |
| 1M NaOH solution in water | 3.20 g |
| 0.75 wt % Arquad 2HT in water | 9.0 g |
| Desmodur VLR20 | 0.78 g |
| Aminosilane-treated kaolin (5 wt % in water) | 29.25 g |
| 25 wt % DETA in water | 1.13 g |

Analysis of these capsules by laser diffraction (Malvern Mastersizer S) showed them to have a median size of 44 μm. As previously, a 1 g sample of the capsule suspension was then mixed with 3.75 g of isopropanol, and after shaking the suspension was split into two parts for leakage analysis immediately and after 24 hours. The percentage of the fragrance that had leaked from the capsules in each sample was calculated, and is shown in Table 4.

TABLE 4

| Sample | % Fragrance leaked in IPA immediately | % Fragrance leaked in IPA after 24 hrs |
|---|---|---|
| Single walled capsules | 5.3% | 95.8% |
| Double-walled capsules | 15.1% | 59.8% |

Upon formation of the double-walled capsules, the immediate leakage of fragrance is seen to have risen slightly, which is attributed to the rupture of some capsules by the high shear process required to coat them with the second layer of polyisocyanate and to redisperse them. However, the 24 hr leakage, and particularly the difference between the two values, is greatly reduced, which demonstrates the reduced permeability of the capsule wall to the fragrance.

Example 2

Single-walled polyurethane capsules containing an aromatic oil (Solvesso 200ND, ExxonMobil) were synthesised by the procedure described in Example 1, using the quantities outlined in Table 5. Analysis by laser diffraction showed the capsules had a median size of approximately 20 µm.

TABLE 5

| | |
|---|---|
| Solvesso 200ND | 34.2 g |
| Desmodur VLR20 | 3.8 g |
| Aminosilane-treated kaolin (5 wt % in water) | 47.4 g |
| Water | 9.5 g |
| 1,5 Pentanediol | 4.1 g |
| 2,2-Bis(hydroxymethyl) Propionic Acid (DMPA) - 25 wt % solution in water | 8.3 g |
| 1,4-diazabicyclo[2.2.2]octane (DABCO) - 20 wt % solution in water | 1.0 g |

A 20 g sample of these capsules was then used to prepare double-walled capsules, again by the procedure described in Example 1, using the quantities shown in Table 6. Analysis by laser diffraction showed that the resultant capsules were partially aggregated, but the median size of the unaggregated capsules was approximately 25 µm.

Leakage testing of both sets of capsules was carried out as described in Example 1, with the results shown in Table 7.

Again, for the double-walled capsules the difference between immediate and 24 hr leakage is around half of the value for the single-walled capsules, indicating the reduced permeability of the capsule walls to the core oil.

TABLE 6

| | |
|---|---|
| Single-Walled Capsule suspension | 20.0 g |
| 1M NaOH solution in water | 3.20 g |
| 0.75 wt % Arquad 2HT in water | 9.0 g |
| Desmodur VLR20 | 0.80 g |
| Aminosilane-treated kaolin (5 wt % in water) | 29.25 g |
| 25 wt % DETA in water | 1.15 g |

TABLE 7

| Sample | % oil leaked in IPA immediately | % oil leaked in IPA after 24 hrs |
|---|---|---|
| Single walled capsules | 4.7% | 29.0% |
| Double-walled capsules | 15.5% | 31.7% |

Example 3—Comparative

Example 4 of WO2009/063257 describes the preparation of a "two-layered" capsule suspension. Example 4 of WO2009/063257 was repeated, save that the encapsulated material was a fragrance. According to the electron micrographs shown in WO2009/063257 (see FIG. 4), the second addition of water-dispersable polyisocyanate is seen to lead to the formation of spheres which adhere to the outside of the single-wall capsule. Leakage rates for the single-wall and "two-layered" microcapsules were determined and it was found that the presence of the second "layer" did not lead to a reduction in the leakage of the fragrance from the microcapsules—after 24 hrs in IPA both single-wall and "two-layered" capsules had leaked more than 95% of their contents. It is believed this is because, being formed from spheres rather than a continuous coating on the microcapsules, the second "layer" is highly permeable and, thus, has no effect on leakage.

The invention claimed is:

1. A method for making microcapsules comprising an encapsulated material, said method comprising:
   (a) providing, in an aqueous continuous phase, one or more microcapsules comprising an encapsulated material surrounded by an inner shell comprising a first cross-linked polymer matrix;
   (b) after step (a), rendering an outer surface of the inner shell hydrophobic by adding a surfactant to the aqueous continuous phase;
   (c) after step (b), forming a Pickering emulsion by adding a polymerizable liquid component and a surface-modified inorganic particulate material to the aqueous continuous phase,
   wherein the polymerizable liquid component is immiscible in the aqueous environment, and
   wherein the one or more microcapsules is wetted by the polymerizable liquid component; and
   (d) after step (c), polymerizing the polymerizable liquid component to form an outer shell comprising a second cross-linked polymer matrix formed about the inner shell.

2. A method according to claim 1, wherein the surface of the surface-modified inorganic particulate material is modified with a chemical of the structure X-Y-Z, in which X is a chemical moiety with an affinity for the particle surface, Z is a reactive chemical moiety, and Y is a chemical moiety that links X and Z together.

3. A method according to claim 2, wherein X is an alkoxy silane group.

4. A method according to claim 2, wherein Y is a $C_{2-6}$ alkylene moiety.

5. A method according to claim 1, wherein the inorganic particulate material comprises clay, silica, silicate, marble or talc.

6. A method according to claim 1, wherein the inorganic particulate material is selected from kaolin, bentonite, alumina, limestone, bauxite, gypsum, magnesium carbonate, calcium carbonate, perlite, dolomite, diatomite, huntite, magnesite, boehmite, palygorskite, mica, vermiculite, hydrotalcite, hectorite, hallyosite, gibbsite, kaolinite, montmorillonite, illite, attapulgite, laponite and sepiolite.

7. A method according to claim 1, wherein the inorganic particulate material has a $d_{50}$ of equal to or less than about 10 μm.

8. A method according to claim 1, wherein the inorganic particulate material has a $d_{90}$ of equal to or less than about 2 μm.

9. A method according to claim 8, wherein the inorganic particulate material has a $d_{90}$ of equal to or less than about 1 μm.

10. A method according to claim 1, wherein the second cross-linked polymer matrix is selected from polyurethane, polyurea, polyepoxide, polyamide, polyester, polysulfonamide, polycarbonate and combinations thereof.

11. A method according to claim 1, wherein the surfactant is a cationic surfactant.

12. A method according to claim 1, wherein the outer surface of the inner shell of the microcapsule comprises pendant moieties which become negatively charged under basic conditions.

13. A method according to claim 12, wherein the pendant moieties comprise acid groups, unsaturated carboxylic acid groups, or saturated carboxylic acid groups.

14. A method according to claim 12, wherein the pendant moieties are chemically bonded to the one or more cross-linking agents used in the preparation of the one or more microcapsules provided in (a).

15. A method according to claim 11, wherein the pH of the aqueous environment during addition of the surfactant is equal to or greater than about 10.

16. A method according to claim 1, wherein the encapsulated material is a liquid which is substantially insoluble in water.

17. A method according to claim 16, wherein the encapsulated material comprises an active agent, and wherein the active agent is less than about 1% by weight soluble in water.

18. A method according to claim 1, wherein the first cross-linked polymer matrix is selected from polyurethane, polyurea, polyepoxide, polyamide, polyester, polysulfonamide, and polycarbonate.

19. The method of claim 2, wherein Z is an amine.

* * * * *